(12) United States Patent
Bagwell et al.

(10) Patent No.: US 7,588,168 B2
(45) Date of Patent: Sep. 15, 2009

(54) COMBINATION DISPENSER FOR CARRYING PRODUCT DISPENSERS

(75) Inventors: Alison Salyer Bagwell, Cumming, GA (US); Martin Shamis, Alpharetta, GA (US); Marty Vistins, Alpharetts, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 550 days.

(21) Appl. No.: 11/183,675

(22) Filed: Jul. 18, 2005

(65) Prior Publication Data

US 2007/0012714 A1    Jan. 18, 2007

(51) Int. Cl.
 *A47F 1/00* (2006.01)
(52) U.S. Cl. .............. 221/96; 211/71.01; 211/90.02
(58) Field of Classification Search ............... 221/96; 211/71.01, 90.02
See application file for complete search history.

(56) References Cited

U.S. PATENT DOCUMENTS

| | | | |
|---|---|---|---|
| 1,487,856 A | 3/1924 | Hauserman et al. | |
| 3,219,400 A | 11/1965 | Berquist | |
| 3,506,321 A | 4/1970 | Hampel | |
| 3,514,170 A | 5/1970 | Shewchuk | |
| 3,552,817 A | 1/1971 | Marcolongo | |
| 3,563,624 A | 2/1971 | Stice | |
| 3,743,372 A | 7/1973 | Ruggerone | |
| 3,776,419 A | 12/1973 | Zinkgraf et al. | |
| 3,851,936 A | 12/1974 | Muller | |
| 3,999,818 A | 12/1976 | Schankler | |
| 4,145,769 A | 3/1979 | MacFarlane et al. | |
| 4,280,643 A * | 7/1981 | Cordova et al. | ............. 294/141 |
| 4,616,755 A | 10/1986 | Adolfsson | |
| D307,841 S | 5/1990 | Hanifl | |
| 4,998,984 A | 3/1991 | McClendon et al. | |
| 5,039,002 A | 8/1991 | Spamer | |
| 5,111,939 A | 5/1992 | Schafer | |
| 5,115,916 A | 5/1992 | Beasley et al. | |
| D335,373 S | 5/1993 | Mosior | |
| 5,271,515 A | 12/1993 | Berkheimer et al. | |
| 5,361,937 A | 11/1994 | Wiese | |
| 5,454,634 A | 10/1995 | Herbst et al. | |
| 5,534,346 A | 7/1996 | Robinson et al. | |
| 5,570,808 A | 11/1996 | Tassoni | |
| D385,626 S | 10/1997 | Mosior et al. | |
| 5,680,744 A | 10/1997 | Kramedjian et al. | |
| 5,702,115 A * | 12/1997 | Pool | ............... 280/47.35 |
| 5,775,046 A | 7/1998 | Fanger et al. | |
| 5,819,989 A | 10/1998 | Saraceni | |
| 5,839,771 A * | 11/1998 | DeMars | ............... 294/146 |

(Continued)

OTHER PUBLICATIONS

EPO Search Report, Jul. 19, 2007.

*Primary Examiner*—Gene Crawford
*Assistant Examiner*—Timothy R Waggoner
(74) *Attorney, Agent, or Firm*—Dority & Manning, P.A.

(57) ABSTRACT

A combination dispenser is provided. The combination dispenser includes a frame and a covering product dispenser carried by the frame. The covering product dispenser is configured for dispensing a covering product for use in covering a portion of a body. A wiping product dispenser is carried by the frame and is configured for dispensing a wiping product for use in wiping a body. An application product dispenser is carried by the frame and is configured for dispensing an application product for use in application to a body.

12 Claims, 7 Drawing Sheets

U.S. PATENT DOCUMENTS

| | | |
|---|---|---|
| 5,884,784 A | 3/1999 | Betts, Sr. |
| 6,021,920 A * | 2/2000 | Aldape ............... 221/96 |
| 6,050,657 A | 4/2000 | Hiltzman |
| 6,241,118 B1 | 6/2001 | Tramontina |
| 6,360,885 B1 | 3/2002 | Krueger et al. |
| D458,065 S | 6/2002 | Christian |
| 6,786,341 B2 | 9/2004 | Stinnett et al. |
| 6,863,192 B2 | 3/2005 | Tumlinson |
| 6,905,039 B2 | 6/2005 | Richter et al. |
| 2002/0040912 A1 | 4/2002 | McHugh |
| 2005/0087507 A1 | 4/2005 | Graneto, III |
| 2005/0178764 A1 | 8/2005 | Richter et al. |
| 2005/0236940 A1 | 10/2005 | Rockoff |
| 2005/0242257 A1 * | 11/2005 | Mosbacher et al. ...... 248/309.1 |
| 2007/0012714 A1 | 1/2007 | Bagwell et al. |

* cited by examiner

COMBINATION DISPENSER FOR CARRYING PRODUCT DISPENSERS

BACKGROUND

In healthcare environments, hand washing is considered important in the arena of infection control. Particularly, hand washing in the healthcare setting is employed in order to reduce the transmission of nosocomial infections. Healthcare guidelines often require strict procedures for both hand washing and glove usage when working in a healthcare environment. For example, some healthcare guidelines mandate a hand washing routine that includes a vigorous scrub of a healthcare provider's hands for at least ten seconds followed by a pat dry with a towel. Further, under such guidelines, medical gloves must be worn when contact with a patient's bodily fluids is possible.

Various dispensers are available for the dispensing of products useful in a healthcare environment. For example, product dispensers for the dispensing of wiping products, such as towels, are known. Additionally, dispensers for the dispensing of covering products, such as gloves, are also in use. Further, dispensers for the dispensing of application products, such as soap, gel, and lotion, are also known. These types of dispensers are individual dispensers that may be transported to and from different locations, or these dispensers are fixed at a single location in a pre-operating room or other area.

These conventional dispensers are configured for the dispensing of but a single type of product. For example, a dispenser may be configured for dispensing a wiping product, such as paper towels, for use in drying one's hands or for the cleaning of a surface, but is not configured for dispensing gloves, soap or additional products desirable in a healthcare environment. As a result, several individual independent dispensers for the provision of various products are necessary. This situation is undesirable in that one or more of the individual dispensers may become displaced and/or a user may have to travel to different areas in order to access the various products. Further, several individual dispensers create clutter about the healthcare environment and increase the chances that the product or dispenser will not be replaced or refilled by maintenance personnel due to their spaced apart and/or movable nature.

SUMMARY

Various features and advantages of the invention will be set forth in part in the following description, or may be obvious from the description, or may be learned from practice of the invention.

A combination dispenser is provided for use in the dispensing of various types of products from a single location so as to increase user convenience, serviceability and compliance with applicable healthcare guidelines. The combination dispenser may be used in various environments other than the healthcare field, which is described for sake of example only.

The combination dispenser includes, in one exemplary embodiment, a frame configured for carrying a dispenser for products used in covering a portion of a body. The combination dispenser also includes a wiping product dispenser that is carried by the frame and configured for dispensing a wiping product to be used in wiping a body. Also included in the combination dispenser is an application product dispenser that is carried by the frame and is configured for dispensing an application product to be applied to a body.

Various exemplary embodiments of the combination dispenser as described above exist in which the covering product dispenser may be configured to dispense different types of covering products. For example, the covering product dispenser may be configured to dispense gloves for use in protecting the hands of a healthcare provider. Additionally, a plurality of covering product dispensers may be provided so as to allow for the dispensing of different sized gloves so as to assure the hands of different sized users are adequately protected. In accordance with one exemplary embodiment, the covering product dispenser may be configured to dispense diapers therefrom.

Another exemplary embodiment of the combination dispenser exists as described above in which the wiping product dispenser is configured for dispensing towels. Additionally, a further exemplary embodiment resides in a combination dispenser as previously discussed in which the wiping product dispenser is configured for dispensing baby wipes.

An exemplary embodiment of the combination dispenser as described above exists in which the product for dispensing from the application product dispenser is soap. Alternatively or additionally, a further exemplary embodiment of the combination dispenser exists in which the application product is an alcohol gel. Still further, another exemplary embodiment of the combination dispenser as previously described exists in which at least three application product dispensers are carried by the frame. At least one of the application product dispensers is configured for dispensing soap, at least one of the application product dispensers is configured for dispensing gel, and at least one of the application product dispensers is configured for dispensing lotion.

A further exemplary embodiment of the combination dispenser exists as described above in which the frame is modular so as to be capable of receiving an add-on frame component that is configured for carrying an add-on dispenser. This embodiment allows for versatility of the combination dispenser so that the combination dispenser may be configured in order to include a desired number or type of dispenser. Additionally, the modular capability allows for the add-on frame component that carries the add-on dispenser to be removed or subsequently replaced once the dispensing product is depleted.

An exemplary embodiment of the combination dispenser as discussed above exists in which the covering product dispenser is located above the wiping product dispenser. Additionally or alternatively, a further exemplary embodiment resides in a combination dispenser as previously discussed in which the covering product dispenser is located to the side of the wiping product dispenser.

A combination dispenser in accordance with yet another exemplary embodiment exists as described above in which the covering product dispenser is located above the application product dispenser. Additionally or alternatively, a further exemplary embodiment resides in a combination dispenser as previously discussed where the covering product dispenser is located to the side of the application product dispenser.

An exemplary embodiment of a combination dispenser for use in a healthcare environment is provided that includes a frame and a glove dispenser carried by the frame. The frame also incorporates a towel dispenser and an application product dispenser. The glove dispenser is located with respect to the towel product dispenser and the application product dispenser so as to minimize contamination to the gloves from a user during dispensing of the towels and the application product.

A further exemplary embodiment of the combination dispenser as immediately discussed resides in having the covering product dispenser, wiping product dispenser and application product dispenser carried directly by the frame.

A further exemplary embodiment of a combination dispenser for use in a healthcare environment exists that includes a frame that carries at least two covering product dispensers that are configured for dispensing different sized gloves. A wiping product dispenser also carried by the frame is included and is configured for dispensing paper towels. Additionally, at least three application product dispensers are carried by the frame and are configured for dispensing and holding soap, gel and lotion for use in application to a body. The covering product dispensers are located above or to the side of the at least three application product dispensers.

Further exemplary embodiments exist in a combination dispenser that may be used in any type of environment. For example, a combination dispenser is provided that includes a frame and a covering product dispenser carried by the frame and configured for dispensing a covering product for use in covering a portion of a body. Additionally, the combination dispenser includes a wiping product dispenser carried by the frame and configured for dispensing a wiping product. An application product dispenser is also provided and is carried by the frame and configured for dispensing an application product.

An additional exemplary embodiment exists in a combination dispenser as immediately discussed in which the wiping product dispenser is configured for dispensing a wiping product that may be a dry nonwoven wipe, a pre-moistened nonwoven wipe, or a swab. Also, the application product dispenser may be configured for dispensing an application product that may be cleaning chemicals, sanitizers, disinfectants, or a surface treatment agent.

These and other features, aspects and advantages of the present invention will become better understood with reference to the following description and appended claims. The accompanying drawings, which are incorporated in and constitute part of this specification, illustrate embodiments of the invention and, together with the description, serve to explain the principles of the invention.

BRIEF DESCRIPTION OF THE DRAWINGS

A full an enabling disclosure of the present invention, including the best mode thereof, directed to one of ordinary skill in the art, is set forth more particularly in the remainder of the specification, which makes reference to the appended Figs. in which.

Figure 1:
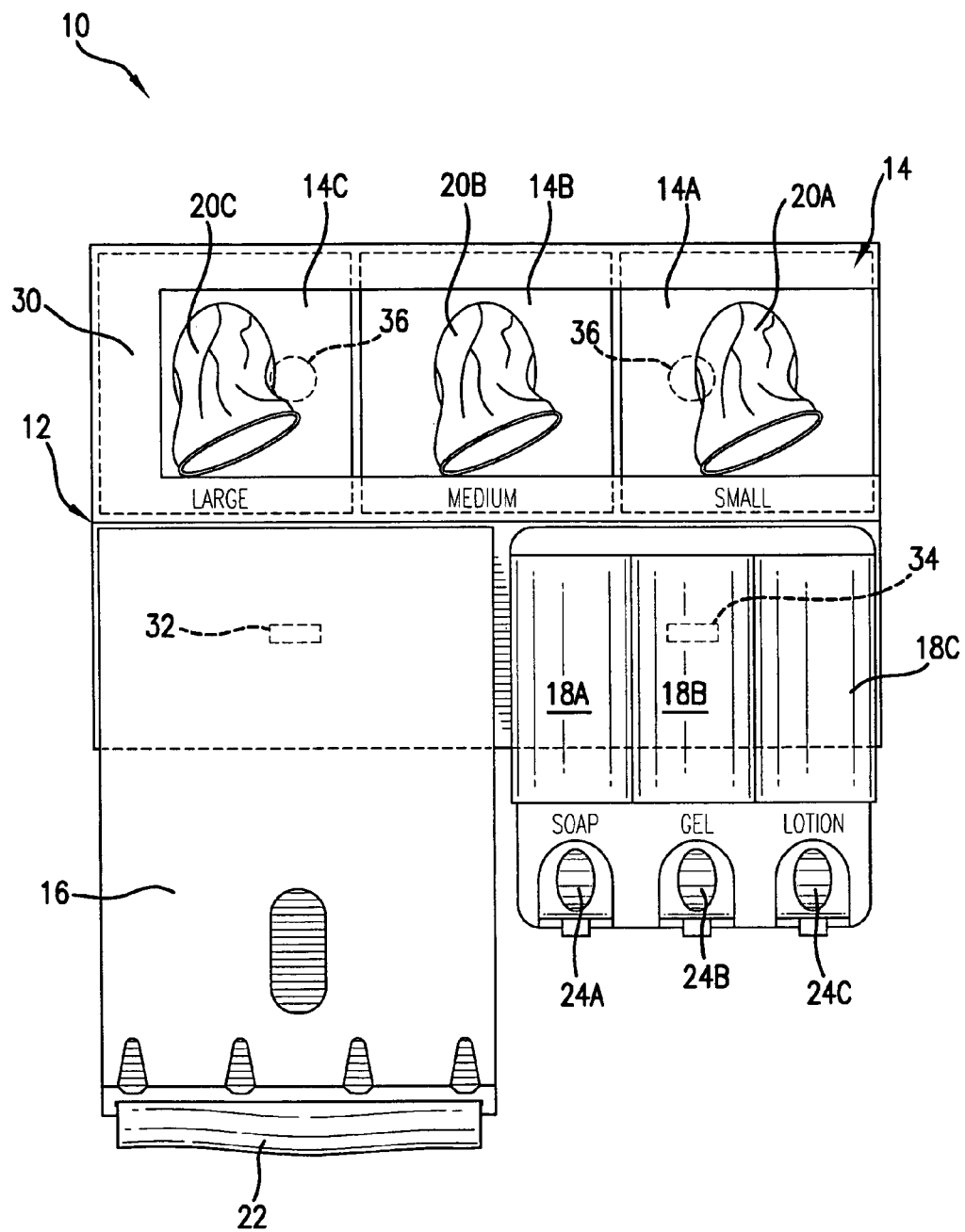
FIG. 1 is a front view of a combination dispenser in accordance with one exemplary embodiment that is configured for the dispensing of towels, soap, gel, lotion and different sizes of gloves.

Repeat use of reference characters in the present specification and drawings is intended to represent the same or analogous features or elements of the invention.

DETAILED DESCRIPTION OF
REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to about 7 also includes a limit of up to about 5, up to about 3, and up to about 4.5.

A combination dispenser 10 is provided that allows for the dispensing of various products from a centralized location. The combination dispenser 10 includes a plurality of product dispensers such as a covering product dispenser 14, a wiping product dispenser 16, and an application product dispenser 18 that are configured for dispensing various types of products that allow for a healthcare provider to comply with healthcare guidelines. The combination dispenser 10 is configured for the dispensing of products such as gloves, towels, soap, gel and/or lotion from a single location so as to reduce the chance that one or more of the product dispensers becomes displaced and to minimize travel of the healthcare provider in accessing various products at different locations. Further, the combination dispenser 10 helps reduce clutter in the healthcare setting and increases serviceability by maintenance personnel due to the centralized location of the various products. The combination dispenser 10 may be configured with different types of products for use in other environments such as alternate care sites, nursing homes and/or surgery centers. Further, the products selected for dispensing from the combination dispenser 10 may be chosen so as to suit the needs of any type of environment. For example, if the combination dispenser 10 were desired to be employed in environments where small children were taken care of, such as daycares, nurseries, PICU and/or NICU, products such as diapers, baby wipes and/or lotions may be dispensed therefrom.

FIG. 1 shows an exemplary embodiment of the combination dispenser 10 wherein the product dispensers 14, 16 and 18 are carried by a frame 12 so as to form the combination dispenser 10 and thus provide for a central location from which products may be dispensed.

The application product dispenser 18 that is included in the combination dispenser 10 may be configured for dispensing any type of application product 24 for use in application to a body. For example, as shown in FIG. 1, three application product dispensers 18A, 18B and 18C are provided. Application product dispenser 18A is configured for the dispensing of application product 24A that is soap. Additionally, application product dispenser 18B is configured for the dispensing of application product 24B that is gel. Finally, application product dispenser 18C is configured for dispensing of application product 24C that is lotion. The application products 24A-24C are housed in respective reservoirs within the application product dispensers 18A-18C and is dispensed from the bottom of the application product dispensers 18A-18C through manual application of a button. The application product dispensers 18A-18C may be provided as an integral unit, although it is to be understood that in accordance with other exemplary embodiments the application product dispensers 18A-18C may be individual units that are individually carried by the frame 12. The application product dispensers 18A-18C may be any one or combination of conventional dispensers commonly known to one having ordinary skill in the art. The configurations shown in FIG. 1 are only exemplary and it is to be understood that other embodiments are possible. For example, the application product dispensers 18A-18C may be configured so as to dispense application products 24A-24C automatically upon the sensing of the hands of a user underneath the application product dispensers 18A-18C.

The soap 24A may be used by the healthcare provider so as to clean his or her hands in order to comply with any applicable healthcare guidelines. The gel 24B may be used by the healthcare provider for use in cleaning his or her hands when cleaning via soap 24A is undesirable due to the absence of a water source. The gel 24B may be an alcohol gel in accordance with one exemplary embodiment that may be desirable for use in cleaning the hands of a healthcare provider so as to reduce the occurrence of skin dermatitis that may result from stripping of the natural oils of the hands of a healthcare provider through frequent hand washing. It is to be understood, however, that any type of gel 24B may be used in accordance with various exemplary embodiments. Lotion 24C may be provided and applied to the skin of a healthcare provider or to the skin of a patient so as to act as a moisturizing agent in order to help prevent drying and cracking of skin. Although the application products 24A-24C have been shown as soap 24A, gel 24B and lotion 24C in the present exemplary embodiment, it is to be understood that the application products 24 may be any type of product capable of being applied to a body in accordance with other exemplary embodiments.

The combination dispenser 10 of FIG. 1 also includes a wiping product dispenser 16 that is carried by the frame 12 and is configured for the dispensing of any type of wiping product 22 for use in wiping of a body. As shown in FIG. 1, the wiping product 22 housed in the wiping product dispenser 16 may be towels 22A to be used for cleaning and drying the hands of a healthcare provider during a hand washing routine per applicable healthcare guidelines. The towels 22A may be housed in a stacked arrangement within the wiping product dispenser 16 and arranged with one another in an interfolded arrangement. The towels 22A may be dispensed from the bottom of the wiping product 16 such that a user will grasp and pull the leading towel 22A so as to remove the leading towel 22A from the wiping product dispenser 16 and present the next towel 22A for subsequent removal. Arrangements of any number of suitable wiping product dispensers 16 are known to one having ordinary skill in the art and it is to be understood that any configuration of the wiping product dispenser 16 may be employed in accordance with various exemplary embodiments. For instance, the wiping product dispenser 16 may be configured so as to include a sensor that detects the presence of the hands of the user so as to cause automatic dispensing of a towel 22A.

The wiping product 22 that may be dispensed from the wiping product dispenser 16 may be selected so as to be any type of product capable for use in wiping a body. For instance, the wiping product 22 may be toilet paper, facial tissues or cloth towels in accordance with other exemplary embodiments.

After cleaning and drying of the hands of a user, healthcare guidelines may require the use of medical gloves by the healthcare provider should contact with a patient's bodily fluids become a possibility. The combination dispenser 10 includes a covering product dispenser 14 for the dispensing of a covering product 20. As shown, three covering product dispensers 14A, 14B and 14C may be provided for the dispensing of three different types of covering products 20A, 20B and 20C which may be three different sizes of gloves. By providing three different sizes of medical gloves 20A-20C the combination dispenser 10 allows for versatility in being used by users having various hand sizes.

The gloves 20A-20C may be housed and dispensed from the covering products dispensers 14A-14C in accordance with any commonly known configuration. For instance, the gloves 20A-20C may be interfolded within the covering product dispensers 14A-14C such that a user will dispense the leading glove 20A-20C therefrom and present the next glove for subsequent use. Additionally, both left and right-handed gloves 20A-20C may be interfolded in the covering product dispensers 14A-14C so that a user will dispense both a right and a left handed glove 20A-20C at the same time. Additionally, the gloves 20A-20C may be universal gloves so that each glove is both "right" and "left" handed. As with the wiping product dispenser 16 and the application product dispenser 18, the covering product dispenser 14 may be variously configured for the dispensing of covering products 20 in accordance with any manner commonly known to one having ordinary skill in the art. The arrangement shown in FIG. 1 is but one example of how the covering products 20A-20C may be dispensed from the covering product dispensers 14A-14C.

Although the exemplary embodiment in FIG. 1 shows the presence of three covering product dispensers 14A-14C, one wiping product dispenser 16 and three application product dispensers 18A-18C, it is to be understood that any number of the various dispensers 14, 16 and 18 may be present in accordance with other exemplary embodiments. For example, three to five covering product dispensers 14, one to three wiping product dispensers 16, and four to seven application product dispensers 18 may be present in accordance with one exemplary embodiment. Further, up to five covering product dispensers 14, wiping product dispensers 16, and application product dispensers 18 may be present in accordance with other exemplary embodiments. As such, various exemplary embodiments are provided in which the combination dispenser 10 may include one or more of the various dispensers 14, 16 and 18.

Although each of the dispensers 14, 16 and 18 are configured for dispensing a single type of product 20, 22 and 24, it is to be understood that other exemplary embodiments exist in which the dispensers 14, 16 and 18 may be configured so as to dispense different types of products 20, 22 and 24. For example, a dispenser may be provided that is capable of dispensing both the wiping product 22 and the application product 24. Alternatively, another exemplary embodiment may exist in which the combination dispenser 10 includes a dispenser that is configured for dispensing both the covering product 20 and the wiping product 22.

Typically, a user will dispense the application products 24A-24C before either the covering products 20A-20C or the wiping product 22. The combination dispenser 10 may be arranged so as to minimize contamination to the application products 24A-24C and/or the wiping product 22. For example, FIG. 1 shows the three covering product dispensers 14A-14C located above both the wiping product dispenser 16 and the three application product dispensers 18A-18C. In this manner, contamination from the hands of a user may be prevented from being transferred to the interior of the covering product dispensers 14A-14C and subsequently to the covering products 20A-20C due to the fact that the user will dispense the application products 24A-24C from a point below the covering products 14A-14C. It may be the case that contamination from the hands of a user would fall during dispensing of the application product 24A-24C and cause contamination of the covering products 24A-24C.

The wiping product dispenser 16 may be located to the side of the application product dispensers 18A-18C. This arrangement also helps minimize contamination to the wiping product 22 because a user's hands will be positioned to the side of the wiping product dispenser 16 when using the application product dispensers 18A-18C. Again, if the wiping product 16 were located below the application product dispensers 18A-18C, dispensing from the application product dispensers 18A-18C could potentially result in contamination from the hands of the user being transferred to the wiping product 22 because the contamination may fall during dispensing and subsequently contact and contaminate the wiping product 22.

The arrangement in FIG. 1 of the combination dispenser 10 may also be advantageous in that contamination on the hands of the user may be prevented from being transferred to the covering products 20A-20C when the user dispenses from the wiping product dispenser 16. Contact with the covering products 20A-20C may be avoided upon dispensing the wiping product 22 because the wiping product 22 is located below the covering products 20A-20C. Again, if the wiping product dispenser 16 were located above the covering product dispensers 14A-14C, it may be the case that contamination will fall from the hands of the user during dispensing of the wiping product 22 and subsequently contaminate the inside of the covering product dispensers 14A-14C and/or the covering products 20A-20C. Typically, the user will dispense from the application product dispenser 18 and then from the wiping product dispenser 16 and finally from the covering product dispenser 14. By placing the covering product dispenser 14 above both the wiping product dispenser 16 and the application product dispenser 18, contamination to the covering product dispensers 14A-14C and the covering products 20A-20C may be avoided.

The combination dispenser 10 may be configured for including dispensers 14, 16 and 18 that are configured only for the dispensing of, and not the storage of, products. In this manner, the combination dispenser 10 may be provided so that storage space of used products is not present. Doing so will prevent potentially contaminated products such as used towels, gloves and diapers from being placed in proximity to the products 20, 22 and 24 in the combination dispenser 10 thus minimizing the risk of contamination to the products 20, 22 and 24. However, it is to be understood that in accordance with certain exemplary embodiments, the combination dispenser 10 may be provided with a storage space for the disposal of used products from the combination dispenser 10 or other products in the healthcare environment.

The product dispensers 14, 16 and 18 may be carried by the frame 12 of the combination dispenser 10 in any suitable manner. As such, various mechanisms exist for carrying the product dispensers 14, 16 and 18 by the frame 12 and it is to be understood that the described mechanisms are only exemplary. FIG. 1 shows a bracket 30 for holding the covering product dispensers 14A-14C to the frame 12. The bracket 30 may be opened on one or more ends such that the covering product dispensers 14A-14C are slid therethrough and positioned as shown in FIG. 1. A wall (not shown) may be slid into place on one or more ends of the bracket 30 so as to insure the covering product dispensers 14A-14C are held therein. Once the covering products 20A-20C are depleted in one or more of the covering product dispensers 14A-14C, the dispensers 14A-14C may be slid out of the bracket 30 and replaced with a new dispenser 14A-14C for further use of the combination dispenser 10.

The frame 12 in FIG. 1 is provided as a metal plate. An attachment 32 is provided so as to attach the wiping product dispenser 16 to the frame 12. Additionally, an attachment 34 is provided for use in attaching the application product dispensers 18A-18C to the frame 12. The attachments 32 and 34 may be of any type commonly known to one having ordinary skill in the art. For instance, the attachments 32 and 34 may be effected through hook and loop type fasteners, brackets and/or snap fit connections. As such, the combination dispenser 10 includes various mechanisms in which the dispensers 14, 16 and 18 may be carried by the frame 12. Additionally, the dispensers 14, 16 and 18 may be removably carried by the frame 12 or the dispensers 14, 16 and 18 may be permanently carried by the frame 12. Additionally, various combinations may be realized in accordance with other exemplary embodiments. For instance, in accordance with one exemplary embodiment the covering product dispenser 14 may be removably carried by the frame 12 while the wiping product dispenser 16 and the application product dispenser 18 are permanently carried by the frame 12.

The combination dispenser 10 may be provided with a wall attachment 36 for use in attaching the combination dispenser 10 to a wall or other supporting structure located in the healthcare environment. As such, the combination dispenser 10 may be positioned on a wall at a height convenient for a user. The wall attachment 36 may be of any type capable of effecting attachment between the combination dispenser 10 and the wall. For instance, the wall attachment 36 may be a receptacle for receiving a bolt or other projection from the wall. Further, the wall attachment 36 may be a pair of brackets through which a mechanical fastener such as a screw, bolt or nail is driven into the wall or other surface so as to retain the combination dispenser 10 thereon.

Figure 2:
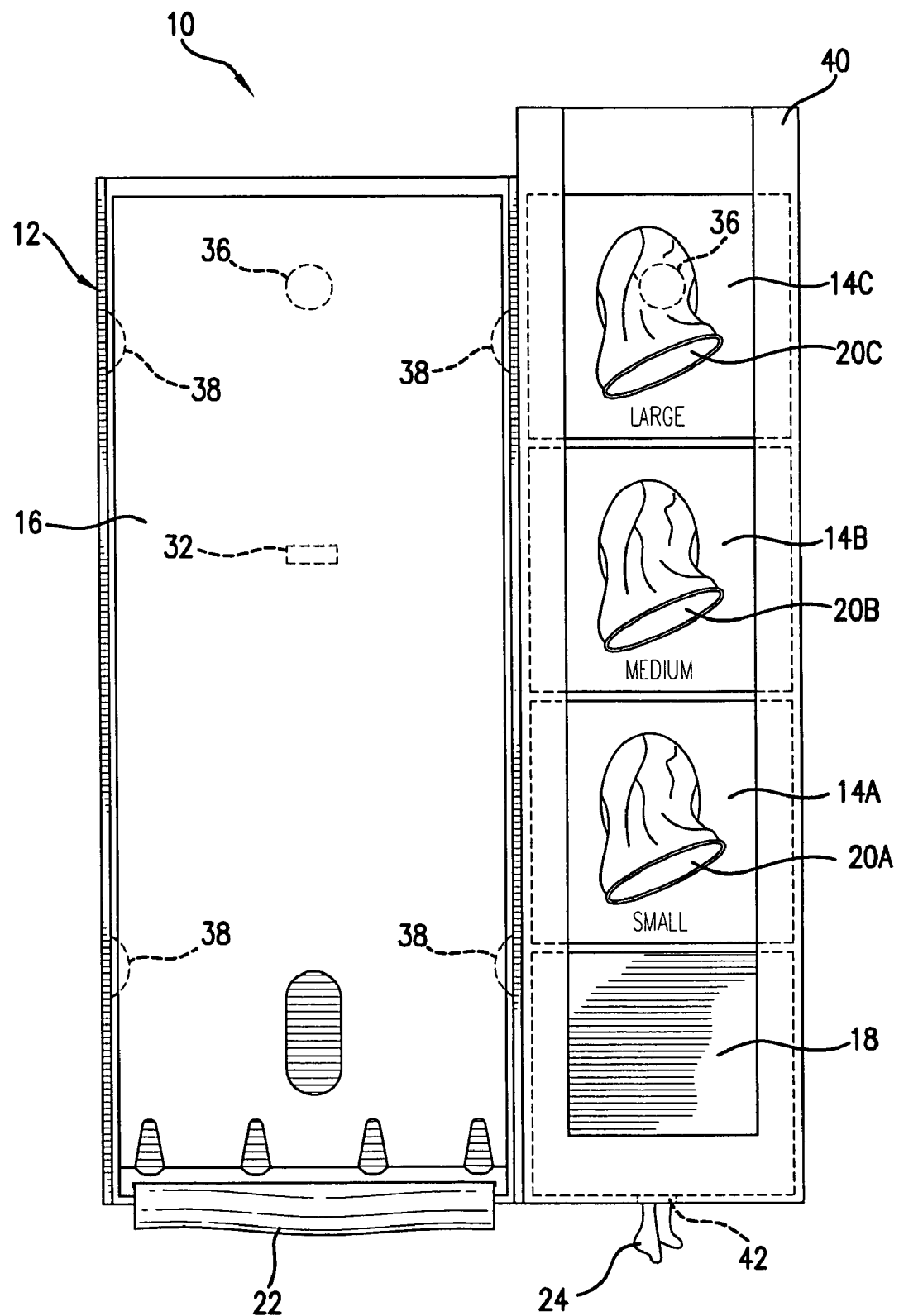
FIG. 2 is a front view of a combination dispenser in accordance with an alternative exemplary embodiment.

FIG. 2 shows an alternative exemplary embodiment of the combination dispenser 10 in which the wiping product dispenser 16 is located to the side of the application product dispenser 18 and the covering product dispensers 14A-14C. Again, the covering product dispensers 14A-14C are located above the application product dispenser 18 so as to minimize contamination to the covering product dispensers 14A-14C. Here, however, the wiping product dispenser 16 is located to the side of the covering product dispensers 14A-14C. This arrangement will also help to reduce contamination to or from the wiping products 22 and the covering products 20A-20C since the dispensers 14 and 16 are located to the side of one another. Still further, the actual dispensing location of the wiping product dispenser 16 is located below the dispensing location of the covering product dispensers 14A-14C so as to prevent contamination from falling when dispensing the wiping product 22 and contaminating the covering products 20A-20C.

In the exemplary embodiment shown in FIG. 2, the covering product dispensers 14A-14C are again configured so as to dispense three different sizes of gloves 20A-20C. The application product 24 and may be soap or moist towelets. The frame 12 includes a bracket 40 that is configured for carrying both the application product dispenser 18 and the three covering product dispensers 14A-14C. The dispensers 14A-14C and 18 are stacked on top of one another such that the application product dispenser 18 is located at the lower most point. A bottom opening 42 is defined in the bracket 40 so as to allow for a dispensing opening through which the application product 24 may be removed from the application product dispenser 18. The covering product dispensers 14A-14C are configured so as to have dispensing openings that coincide with a dispensing opening defined in the bracket 40. As such, a user of the combination dispenser 10 may dispense the covering products 20A-20C from the front of the combination dispenser 10, and the user of the combination dispenser 10 may dispense the application product 24 from the bottom thereof.

The wiping product 22 may be a plurality of paper towels that are stacked in an interfolded arrangement within the wiping product dispenser 16. One such exemplary embodiment of a wiping product dispenser 16 and associated towels 22 may be found in U.S. Pat. No. 6,241,118 issued to Tramontina that issued on Jun. 5, 2001 and is incorporated by reference herein in its entirety for all purposes. With this type of wiping product dispenser 16, a plurality of protrusions 38 are defined on the frame 12 and are configured for being received in various openings of the wiping product dispenser 16 so as to engage and hold the stack of wiping products 22 therein. The wiping product dispenser 16 may be carried by the frame 12 through any attachment mechanism commonly known to one having ordinary skill in the art. For example, the frame 12 may be configured so as to define a receiving cavity into which the wiping product dispenser 16 may be force fit so as to be retained onto the frame 12. Additionally or alternatively, the protrusions 38 on the frame 12 may also act to hold the wiping product dispenser 16 so as to cause the wiping product dispenser 16 to be retained on the frame 12.

Figure 3:
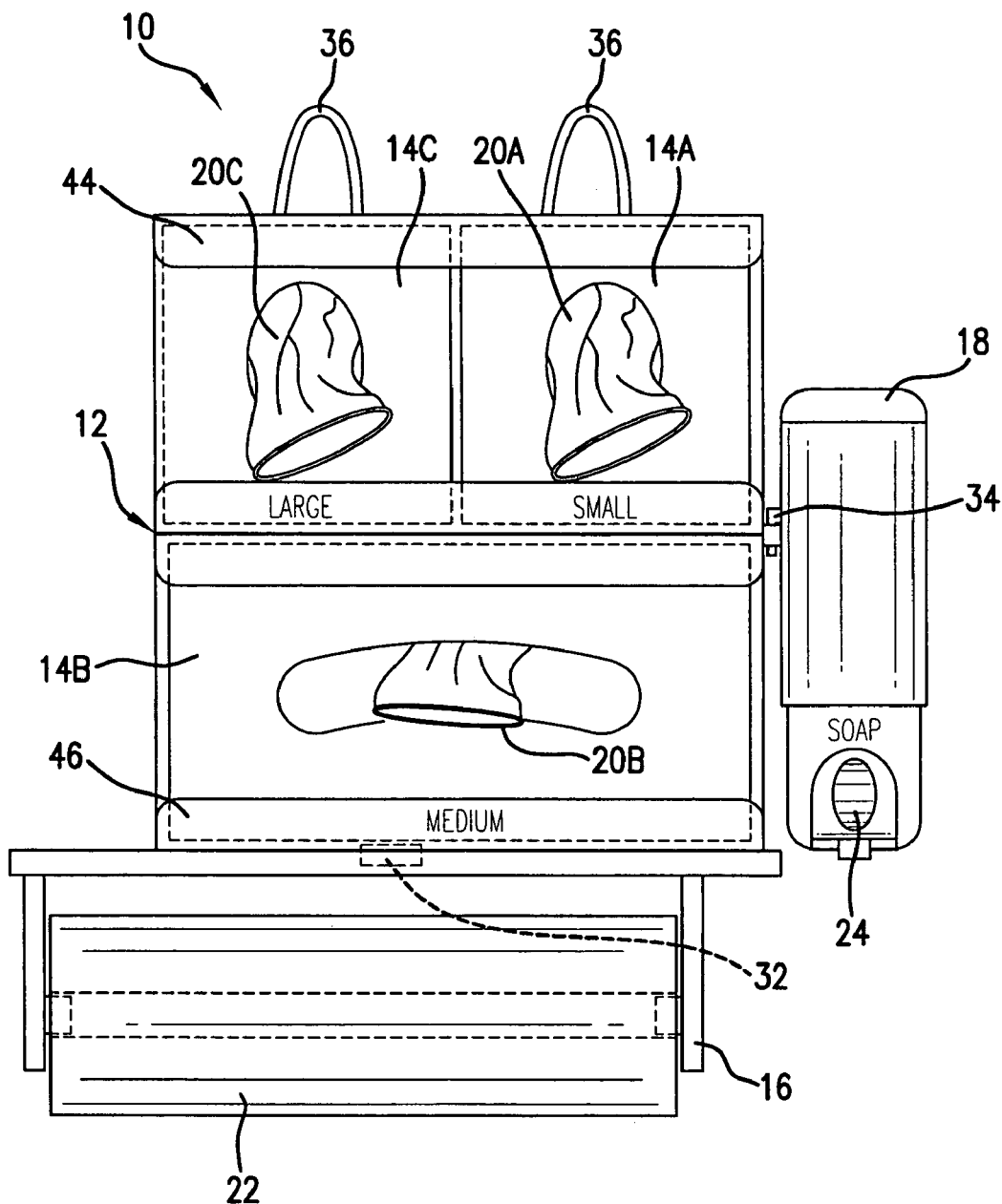
FIG. 3 is a front view of a combination dispenser in accordance with another alternative exemplary embodiment.

FIG. 3 shows an alternative exemplary embodiment of the combination dispenser 10 in which the covering product dispensers 14A-14C are again positioned so as to minimize contamination to and from the dispensers 14A-14C and an application product dispenser 18. In this regard, the covering product dispensers 14A-14C are positioned to the side of the application product dispenser 18. Likewise, the dispensing location of the application product dispenser 18 is located below the dispensing locations of the covering product dispensers 14A-14C so as to further minimize the chance of contamination being transferred to the covering product dispensers 14A-14C and associated covering products 20A-20C upon a user dispensing application product 24 from the dispenser 18.

In the exemplary embodiment shown in FIG. 3, the covering product dispensers 14A-14C are configured so as to dispense different sized and styled gloves 20A-20C. Small sized gloves 20A are dispensed by a covering product dispenser 14A that is carried by a bracket 44. Likewise, large sized gloves 20C that are dispensed from the covering product dispenser 14C are also held by the bracket 44. The bracket 44 may be opened on one or more ends so as to slide the covering product dispensers 14A and 14C thereon. Subsequently, the covering product dispensers 14A and 14C may be prevented from sliding out of the bracket 44 through any means commonly known to one having ordinary skill in the art.

A bracket 46 is provided below the bracket 44 and is configured for holding the covering product dispenser 14B that is likewise configured for dispensing of the gloves 20B. The gloves 20B may be medium sized gloves and may be provided in greater number since it may be the case that users of the combination dispenser 10 will typically be in greater need of a medium sized glove 20B. The style of the gloves 20B may be different than the style of the gloves 20A and 20C, although in accordance with other exemplary embodiments all of the gloves 20A-20C are of the same style. In accordance with one exemplary embodiment, the gloves 20B may be a powder free textured latex exam glove. Again, the bracket 46 may be configured so as to be closable on one or either ends so as to help retain the covering product dispenser 14B thereon. Alternatively, the bracket 46 may be open on one or more ends.

The application product dispenser 18 is configured for holding soap 24. The soap 24 is dispensed from a dispensing mechanism of the application product dispenser 18 similar to that previously described with respect to the exemplary embodiment in FIG. 1. The wiping product 22 is positioned to the side of the application product dispenser 18 so as to minimize the chance of contamination of the wiping products 22 when a user dispenses soap 24 from the application product dispenser 18. Again, if the wiping product 22 was positioned under the application product dispenser 18, contamination of the hands user may fall and thus be subsequently transferred to and contaminate the wiping product 22.

The wiping product 22 shown in FIG. 3 is a roll of cored paper towels that are held by the wiping product dispenser 16 in a commonly known arrangement. In accordance with other exemplary embodiments, the towels 22 may be configured into a coreless roll for dispensing. Various examples of different configurations of wiping product dispenser 16 and wiping product 22 arrangements are shown and described in U.S. Pat. No. 6,360,885 issued to Phelps, et al. that issued on Mar. 26, 2002 and is incorporated by reference herein in its entirety for all purposes. The towels 22 are located below the gloves 20A-20C so as to minimize the chance of contamination present on a user's hands from being transferred to the gloves 20A-20C when the user dispenses one of the towels 22.

The frame 12 in FIG. 3 may be a metal plate sized so as to hold the covering product dispensers 14A-14C on the front surface thereof. The application product dispenser 18 may be attached to the side of the frame 12 by an attachment 34. The wiping product dispenser 16 may be attached to the bottom of the frame 12 by the attachment 32 so that both the application product dispenser 18 and wiping product dispenser 16 are carried by the frame 12. The frame 12 may be made of a metal, such as aluminum or steel, or the frame 12 may be made out of a laminate or plastic material in accordance with various exemplary embodiments.

Figure 4:
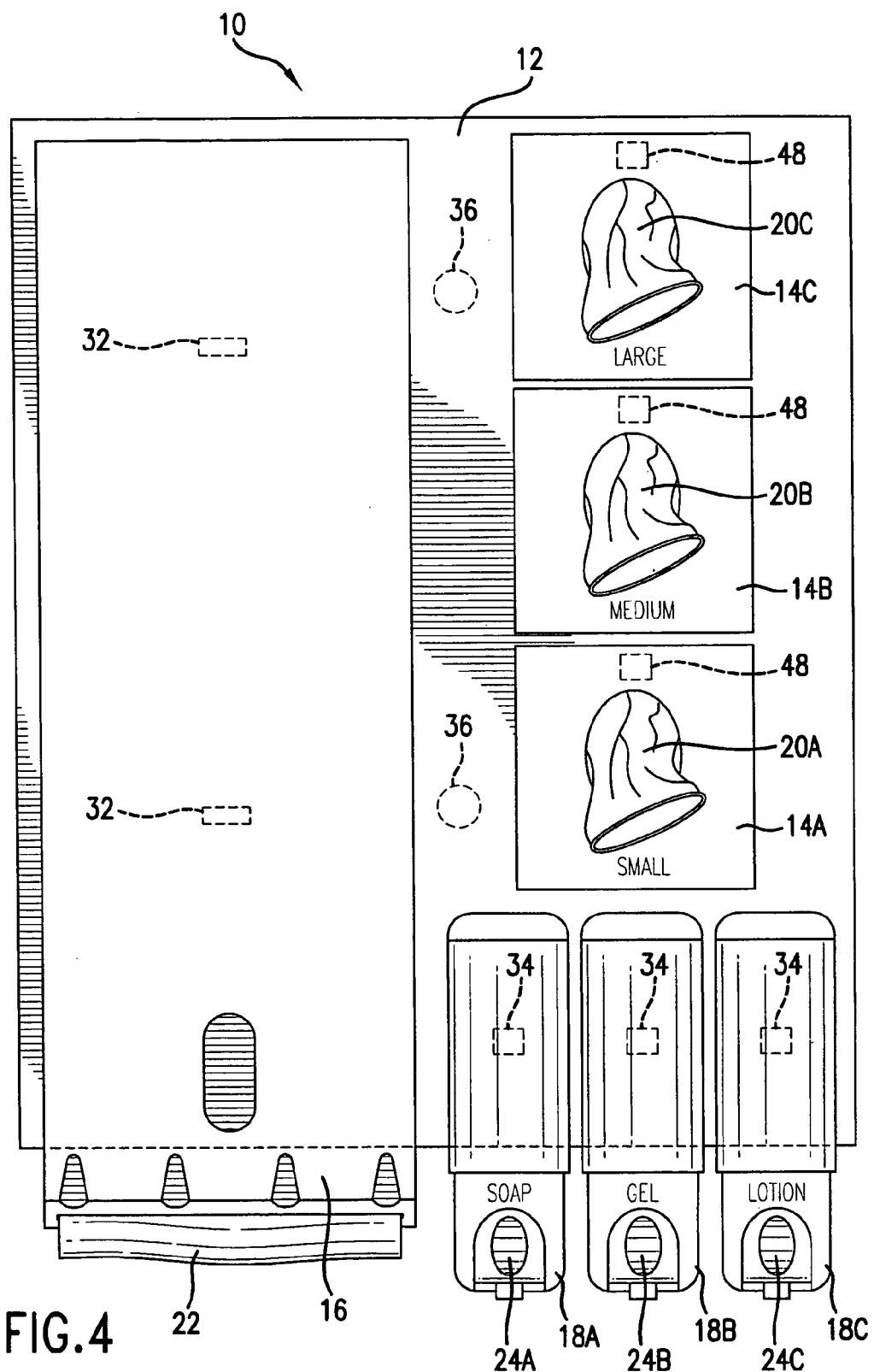
FIG. 4 is a front view of a combination dispenser in accordance with yet another alternative exemplary embodiment.

FIG. 4 shows another alternative exemplary embodiment of the combination dispenser 10. Again, the frame 12 includes a plate that is generally flat and has the dispensers 14, 16 and 18 located on one surface thereof. A single wiping product dispenser 16 is present in the combination dispenser 10 of FIG. 4 and is attached to the frame 12 by attachments 32 so as to be carried thereon. Three covering product dispensers 14A-14C configured for dispensing variously sized gloves 20A-20C are also present and are positioned to the side of the wiping product dispenser 16. Each of the covering product dispensers 14A-14C are individually attached to the frame 12 by way of individual attachments 48. Also individually attached to the frame 12 are a plurality of application product dispensers 18A-18C that are attached through individual attachments 34 so as to be carried by the frame 12. The application product dispensers 18A-18C are configured for the dispensing of soap 24A, gel 24B and lotion 24C. The application product dispensers 18A-18C are located below the covering product dispensers 14A-14C and are located to the side of the wiping product dispenser 16 so as to minimize contamination to the towels 22 and the gloves 20A-20C. The dispensers 14, 16 and 18 are individually attached to the frame 12 so that they may be removed therefrom and replaced with a new dispenser 14, 16 or 18 once the product contained therein is depleted.

Figure 5:
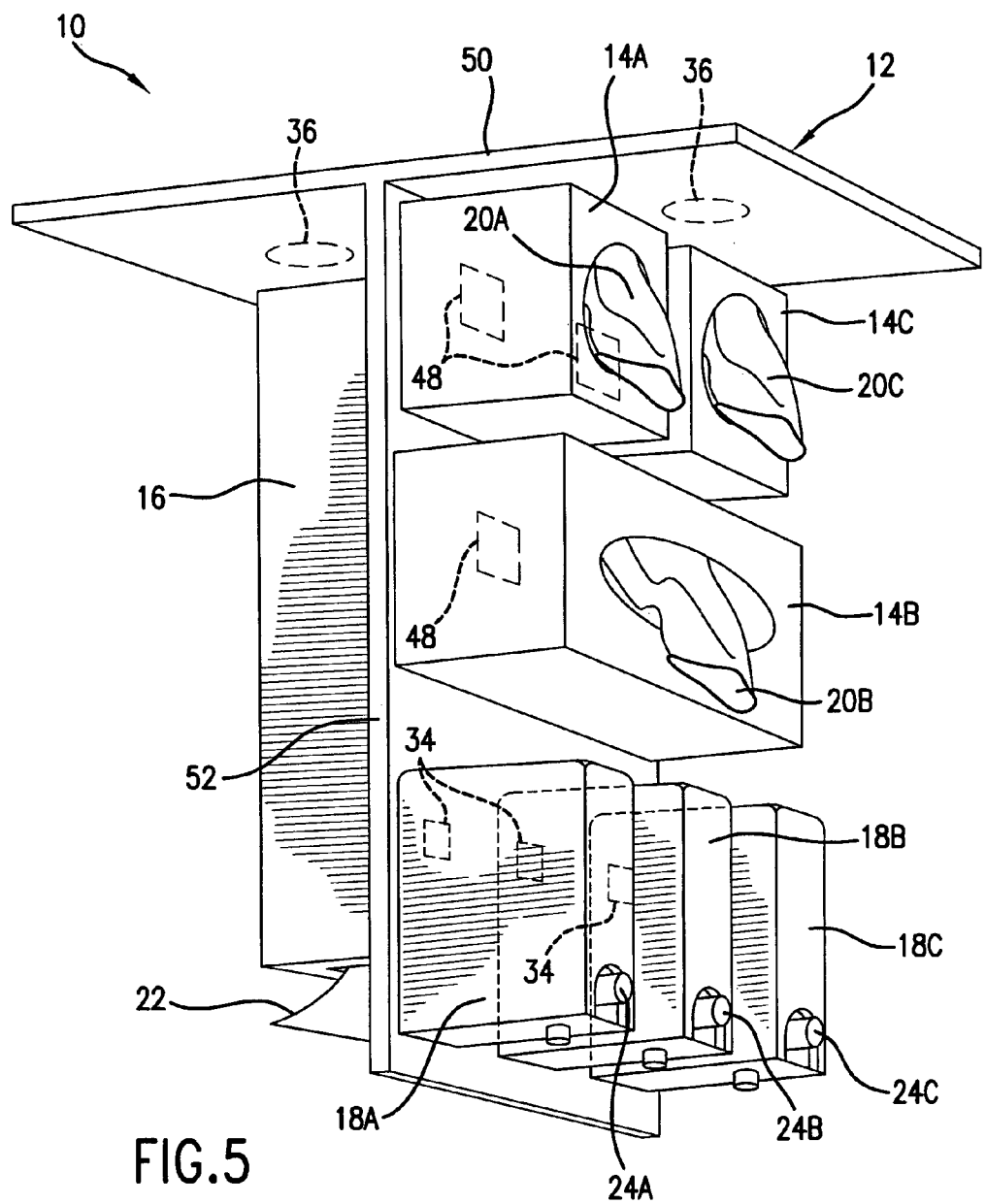
FIG. 5 is a perspective view of a combination dispenser in accordance with one exemplary embodiment.

FIG. 5 shows another alternative exemplary embodiment of the combination dispenser 10 in which the combination dispenser 10 is configured for attachment to a horizontal surface through way of attachments 36. The frame 12 may be constructed in a variety of manners. Although previously described as being primarily in the shape of a plate, the frame 12 may be configured so as to be rectangular, spherical, circular or triangular in shape in accordance with various exemplary embodiments. It is to be understood that the frame 12 is a structure that is configured for carrying the dispensers 14, 16 and 18 and is not limited to a particular style, material, or configuration. As shown in FIG. 5, the frame 12 includes an upper frame section 50 and a lower frame section 52 that are assembled in a "T" shape arrangement. Three covering product dispensers 14A-14C are again provided and are configured for dispensing gloves 20A-20C. The covering product dispensers 14A-14C are carried on the lower frame section 52 through attachments 48. On the same side of the lower frame section 52 that the covering product dispensers 14A-14C are provided, three application product dispensers 18A-18C configured for dispensing soap 24A, gel 24B and lotion 24C are included through attachments 34. Again, the covering product dispensers 14A-14C are located above the application product dispensers 18A-18C.

A wiping product dispenser 16 for the dispensing of towels 22 is located on the reverse side of the lower frame section 52. Again, the wiping product dispenser 16 is located to the side of the application product dispensers 18A-18C so as to minimize the chance of contamination therebetween. In this case, the wiping product dispenser 16 is situated so as to be in back of the application product dispensers 18A-18C.

Figure 6:
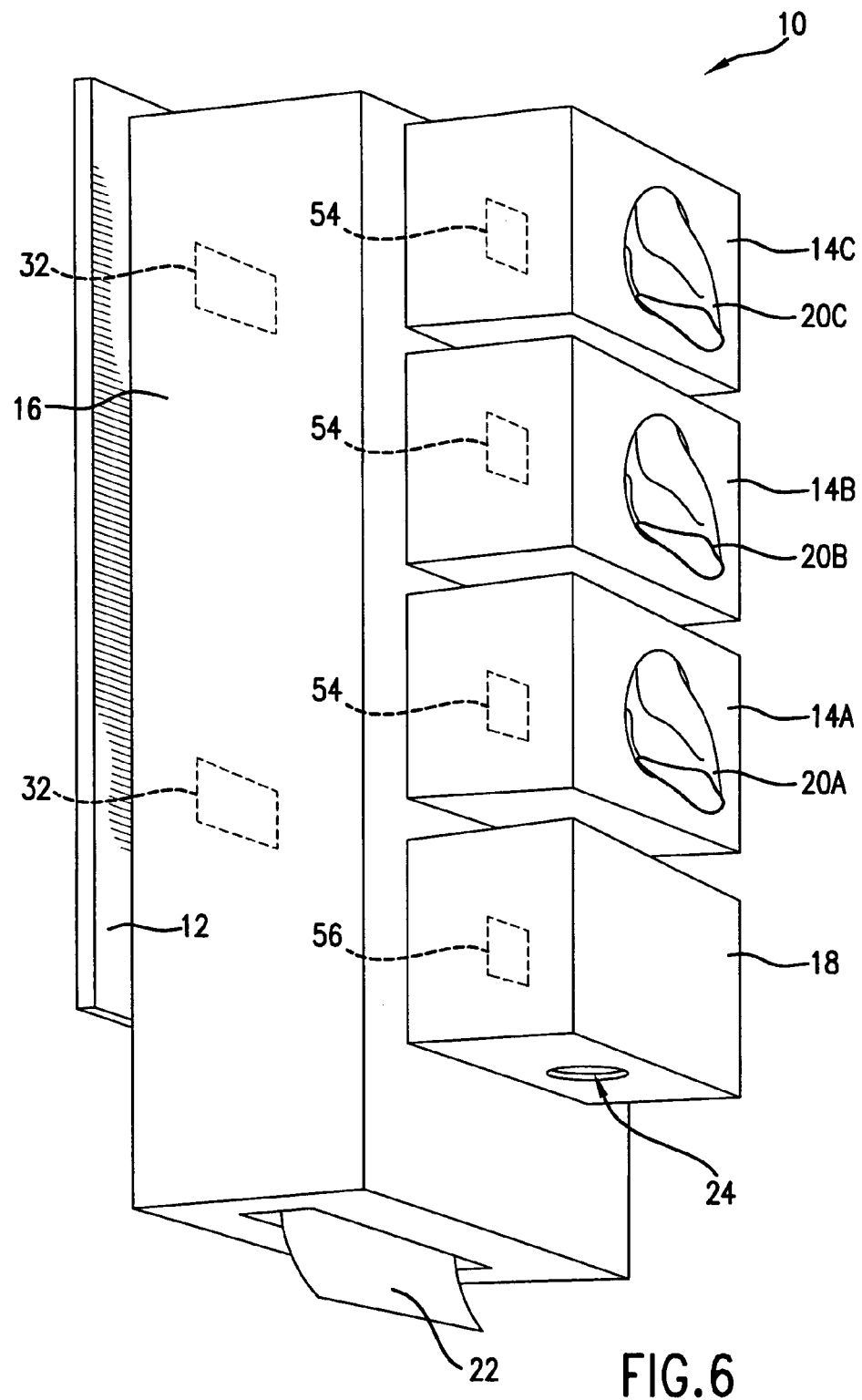
FIG. 6 is a perspective view of a combination dispenser in accordance with yet another alternative exemplary embodiment.

Another exemplary embodiment of the combination dispenser 10 is shown in FIG. 6 in which the frame 12 is configured so as to be "side" mounted to a wall or other surface. The wiping product dispenser 16 is directly attached to the frame 12 through attachments 32. The covering product dispensers 14A-14C and the application product dispenser 18 are indirectly attached to the frame 12. In this instance, the covering product dispensers 14A-14C are attached to the wiping product dispenser 16 through dispenser attachments 54. Additionally, a dispenser attachment 56 is provided for effecting attachment between the application product dispenser 18 and the wiping product dispenser 16. In this manner, the covering product dispensers 14A-14C and the application product dispenser 18 are carried by the frame 12 such that these components are indirectly carried by the frame 12. In contrast, the wiping product dispenser 16 is directly carried by the frame 12 due to the direct attachment of these two components by attachments 32.

Again, the application product dispenser 18 may be positioned below the covering product dispensers 14A-14C and to the side of the wiping product dispenser 16. Specifically, the application product dispenser 18 is positioned in front of the wiping product dispenser 16. The application product dispenser 18 may be configured for dispensing soap or moist towelets in accordance with the exemplary embodiment shown in FIG. 6.

Figure 7:
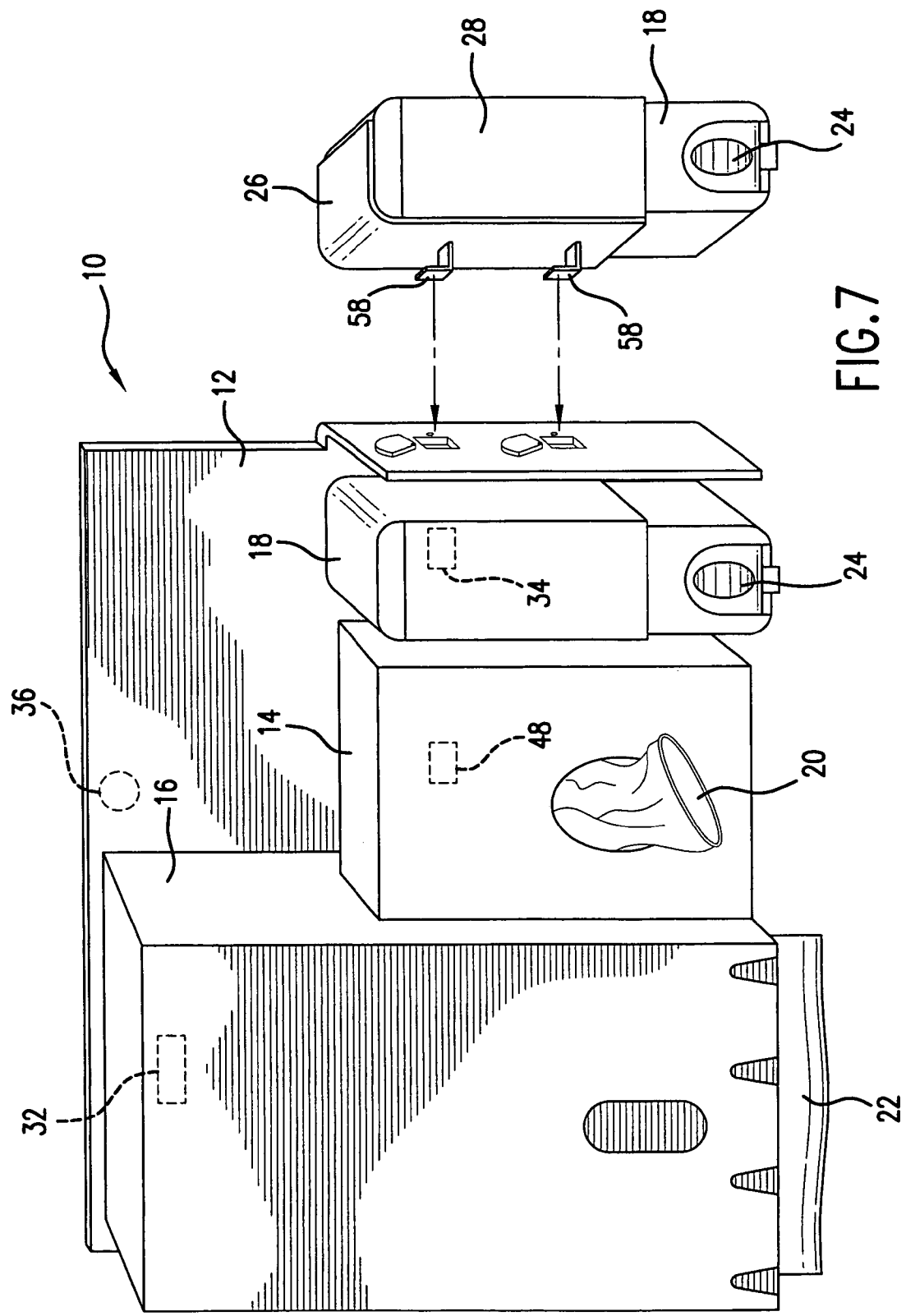
FIG. 7 is a perspective view of a combination dispenser that includes a frame with an add-on feature that is configured for receiving and carrying an add-on frame component with an add-on dispenser in accordance with another exemplary embodiment.

FIG. 7 shows an exemplary embodiment of the combination dispenser 10 that includes but a single covering product dispenser 14, wiping product dispenser 16 and application product dispenser 18. The covering product dispenser 14 is configured for the dispensing of gloves 20 while towels 22 and soap 24 are dispensed from the other dispensers 16 and 18. The dispensing location of the gloves 20, towels 22 and soap 24 are positioned to the side of one another so as to minimize the chance of contamination therebetween.

The frame 12 of the combination dispenser 10 in FIG. 7 includes an add-on feature to provide for a combination dispenser 10 that is modular in nature. An add-on frame component 26 may be provided and may be capable of being carried by the frame 12 so as to increase the functionality of the combination dispenser 10. In this instance, the add-on frame component 26 includes an add-on dispenser 28 that is configured for the dispensing of a product, such as a different type of soap, that may be useful in a healthcare environment. A pair of mechanical attachments 58 are included so as to allow the add-on frame component 26 to engage the frame 12 and then be held securely thereon. The attachment 58 is configured so as to have projections extending from the add-on frame component 26 received within recesses in the frame 12. A pair of swivels may be swung and locked into place so as to retain the add-on frame component 26 to the frame 12. As can be imagined, the frame 12 may be provided so as to be capable of receiving or disengaging various components onto which different dispensers may or may not be located so as to adapt the combination dispenser 10 for various desired uses. Additionally, modularity of the combination dispenser 10 may be desirable should one of the dispensers become disabled or depleted of product. In this instance, the add-on frame component 26 may be disengaged from the frame 12 and thrown away while a new add-on frame component 26 may be attached to the frame 12 if desired.

Although described as being used in the healthcare environment, the combination dispenser 10 may be configured so as to be adaptable to other situations. For instance, the combination dispenser 10 may be modified so as to be useful in an industrial type of environment in which industrial gloves 20 and harsher soaps 24 may be dispensed. The combination dispenser 10 may be used for surface cleaning or other surface treatment for manufacturing, food services, and automobile businesses. The wiping product 22 may be dry or pre-moistened nonwoven wipes, and/or swabs in accordance with various exemplary embodiments. Additionally, the application product 24 that may be dispensed may be cleaning chemicals, sanitizers, disinfectants, and other types of surface treatment agents. As such, the combination dispenser 10 may be used in any type of environmental application.

The covering product 20 may be any type of covering product for use in covering a portion of a body. Although described for sake of example as relating to items used in the healthcare environment, it is to be understood that other covering products 20 useful in other environments are possible. Representative examples of covering products 20 that may be dispensed from the combination dispenser 10 include medical gloves, diapers, industrial gloves, adult incontinence products, sanitary napkins, condoms or other prophylactics, drapes, gowns, and/or face masks. It is to be understood that the aforementioned list is only representative of and not a comprehensive listing of the covering products 20 that may be included in the combination dispenser 10.

Likewise, various type of wiping products 22 may be dispensed and may be selected so as to be useful in environments other than healthcare environments. Representative examples of wiping products 22 include paper towels, cloth towels, toilet tissue, facial tissue, baby wipes, napkins, sponges, and/or foam pads. Again, the aforementioned list provides examples of wiping products 22 and it is to be understood that other specific types of wiping products 22 are present in accordance with other exemplary embodiments.

Application products 24 that may be employed in accordance with various exemplary embodiments include liquid soap, granular soap, gel such as alcohol gel, lotion, moist towelets, spermicidal cream or other prophylactics, paint, polish, medication and/or shampoo. The aforementioned list is only representative of particular examples of the application product 24 and it should be understood that other types of application products 24 are present in other exemplary embodiments.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed:

1. A combination dispenser, comprising:
    a frame with mounting structure so that said frame is configured for vertical mounting on a support surface;
    a covering product dispenser carried by said frame and configured for dispensing a covering product for use in covering a portion of a body;
    a wiping product dispenser carried by said frame and configured for dispensing a wiping product for use in wiping a body;
    an application product dispenser carried by said frame and configured for dispensing an application product for use in application to a body;
    in order of use by a user, said application product is used first, followed by said wiping product, followed by said covering product;
    wherein said application product dispenser is oriented at a vertical position on said frame below said covering product dispenser and said wiping product dispenser is oriented at a vertical position on said frame no higher than said covering product dispenser so as to minimize contamination of said covering products during dispensing of said application product and said wiping product;
    wherein said covering product dispenser is located to the side of said wiping product dispenser; and
    wherein said frame comprises a vertically extending lower frame section that separates said covering product dispenser from said wiping product dispenser, and an upper frame section configured for mounting on a ceiling support surface, said lower frame section extending from said upper frame section.

2. The combination dispenser as in claim 1, wherein said covering product dispenser is configured as a glove dispenser.

3. The combination dispenser as in claim 1, wherein said wiping product dispenser is configured as a towel dispenser.

4. The combination dispenser as in claim 1, wherein said application product dispenser is configured as a soap dispenser.

5. The combination dispenser as in claim 1, wherein said application product dispenser is configured as an alcohol gel dispenser.

6. The combination dispenser as in claim 1, wherein a plurality of said covering product dispensers are carried by said frame, and wherein said plurality of covering product dispensers are configured for dispensing different sized gloves.

7. The combination dispenser as in claim 1, wherein at least three of said application product dispensers are carried by said frame, and wherein at least one of said application product dispensers is configured for dispensing soap, and wherein at least one of said application product dispensers is configured for dispensing gel, and wherein at least one of said application product dispensers is configured for dispensing lotion.

8. The combination dispenser as in claim 1, wherein said covering product dispenser is configured for dispensing diapers, and wherein said wiping product dispenser is configured for dispensing baby wipes.

9. The combination dispenser as in claim 1, wherein said frame is modular so as to be configured for receiving an add-on frame component that is configured for carrying an add-on dispenser.

10. The combination dispenser as in claim 1, wherein said covering product dispenser is located above said wiping product dispenser.

11. A combination dispenser for use in a healthcare environment, comprising:
    a frame with mounting structure so that said frame is configured for mounting in a vertical orientation on a support surface;
    a covering product dispenser configured for holding a plurality of gloves for use in covering the hands of a body, wherein said covering product dispenser is configured for dispensing said gloves, and wherein said covering product dispenser is carried by said frame;
    a wiping product dispenser configured for holding towels for use in wiping a body, wherein said wiping product dispenser is configured for dispensing said towels, and wherein said wiping product dispenser is carried by said frame;
    an application product dispenser configured for holding an application product for use in application to a body, wherein said application product dispenser is configured for dispensing said application product, and wherein said application product dispenser is carried by said frame;
    in order of use by a user, said application product is used first, followed by said wiping product, followed by said covering product;
    wherein said application product dispenser is oriented at a vertical position on said frame below said covering product dispenser and said wiping product dispenser is oriented at a vertical position on said frame no higher than said covering product dispenser so as to minimize contamination of said covering products during dispensing of said application product and said wiping product; and
    wherein said covering product dispenser is located on the side of said wiping product dispenser such that said covering product dispenser is located in front of and above a dispensing opening in said wiping product dispenser.

12. The combination dispenser as in claim 11, wherein said frame comprises a vertically extending lower frame section that separates said covering product dispenser from said wiping product dispenser.

* * * * *

UNITED STATES PATENT AND TRADEMARK OFFICE
CERTIFICATE OF CORRECTION

PATENT NO. : 7,588,168 B2 Page 1 of 1
APPLICATION NO. : 11/183675
DATED : September 15, 2009
INVENTOR(S) : Bagwell et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 885 days.

Signed and Sealed this

Twenty-first Day of September, 2010

David J. Kappos
*Director of the United States Patent and Trademark Office*